US00PP15942P2

(12) United States Plant Patent
De La Torre

(10) Patent No.: US PP15,942 P2
(45) Date of Patent: Sep. 6, 2005

(54) ***GAZANIA* PLANT NAMED 'CALIFORNIA GOLD'**

(50) Latin Name: *Gazania rigens*
Varietal Denomination: California Gold

(75) Inventor: Jose Jaime De La Torre, Chino, CA (US)

(73) Assignee: Salvador De La Torre, Riverside, CA (US)

( * ) Notice: Subject to any disclaimer, the term of this patent is extended or adjusted under 35 U.S.C. 154(b) by 50 days.

(21) Appl. No.: 10/859,514

(22) Filed: Jun. 1, 2004

(51) Int. Cl.[7] ..... A01H 5/00
(52) U.S. Cl. ..... Plt./263
(58) Field of Search ..... Plt./263

*Primary Examiner*—Anne Marie Grunberg
(74) *Attorney, Agent, or Firm*—C. A. Whealy

(57) ABSTRACT

A new and distinct cultivar of *Gazania* named 'California Gold', characterized by its compact, low-growing and bushy growth habit; upright, outwardly spreading and rounded plant form; freely-flowering habit; large fully inflorescences with yellow and orange bi-colored ray florets; and relatively less susceptible to fungal pathogens common to *Gazanias*.

1 Drawing Sheet

Botanical classification/cultivar designation: *Gazania rigens* cultivar California Gold.

BACKGROUND OF THE INVENTION

The present invention relates to a new and distinct cultivar of *Gazania* plant, botanically known as *Gazania rigens* and referred to by the name 'California Gold'.

The new *Gazania* is a product of a planned breeding program conducted by the Inventor in Ontario, Calif. The objective of the program is to create and develop new *Gazania* cultivars with a compact growth habit and numerous inflorescences with attractive ray floret coloration.

The new *Gazania* originated from a cross-pollination of two unknown selections of *Gazania rigens*, not patented. The new *Gazania* was discovered and selected by the Inventor as a plant within the progeny of the stated cross-pollination in a controlled environment in Ontario, Calif. in March, 2000.

Asexual reproduction of the new *Gazania* by terminal cuttings in a controlled environment in Ontario, Calif. since April, 2000, has shown that the unique features of this new *Gazania* are stable and reproduced true to type in successive generations.

SUMMARY OF THE INVENTION

The new *Gazania* has not been observed under all possible environmental conditions. The phenotype may vary somewhat with variations in environment such as temperature and light intensity without, however, any variance in genotype.

The following characteristics have been repeatedly observed and are determined to be basic characteristics of 'California Gold' and distinguish the new *Gazania* as a new and distinct cultivar:

1. Compact, low-growing and bushy growth habit.
2. Upright, outwardly spreading and rounded plant form.
3. Freely-flowering habit.
4. Large fully inflorescences with yellow and orange bi-colored ray florets.

5. Relatively less susceptible to fungal pathogens common to *Gazanias*.

Plants of the new *Gazania* can be compared to plants of the cultivar Mitsuwa Yellow, not patented. In side-by-side comparisons conducted by the Inventor in Ontario, Calif., plants of the new *Gazania* differed from plants of the cultivar Mitsuwa Yellow in the following characteristics:

1. Plants of the new *Gazania* had slightly narrower leaves than plants of the cultivar Mitsuwa Yellow.
2. Plants of the new *Gazania* were more freely flowering than plants of the cultivar Mitsuwa Yellow.
3. Plants of the new *Gazania* had larger inflorescences with more ray florets per inflorescence than plants of the cultivar Mitsuwa Yellow.
4. Ray florets of plants of the new *Gazania* were yellow and orange bi-colored whereas ray florets of plants of the cultivar Mitsuwa Yellow were yellow in color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Gazania*.

The photograph at the top of the sheet comprises a side perspective view of a typical plant of 'California Gold' grown in a container.

The photograph at the bottom of the sheet comprises a close-up view of typical inflorescences and leaves of 'California Gold'.

DETAILED BOTANICAL DESCRIPTION

The aforementioned photographs and following observations and measurements describe plants grown in Ojai, Calif. during the summer and autumn in an outdoor nursery with day temperatures ranging from 24 to 38° C. and night temperatures ranging from 10 to 18° C. Rooted liners of the new *Gazania* were planted in 15.25-cm containers with three plants per container and had been growing for about three months when the photographs and description were taken. Color references are made to The Royal Horticultural Society Colour Chart, 1995 Edition, except where general terms of ordinary dictionary significance are used.

Botanical classification: *Gazania rigens* cultivar California Gold.

Parentage:

*Female or seed parent.*—Unknown selection of *Gazania rigens*, not patented.

*Male or pollen parent.*—Unknown selection of *Gazania rigens*, not patented.

Propagation:

*Type.*—By cuttings.

*Time to initiate roots.*—Summer: About 10 days at 27 to 32° C. Winter: About two weeks at 18 to 21° C.

*Root description.*—Fine.

*Rooting habit.*—Freely-branching.

Plant description:

*General appearance.*—Compact, low-growing and bushy growth habit; outwardly spreading and rounded plant form with dense foliage and inflorescences held above and beyond the foliage. Moderately vigorous growth habit. Freely branching, about four to five lateral branches per plant.

*Plant height, to top of inflorescences.*—About 17 cm.

*Plant height, to top of foliar plane.*—About 11 cm.

*Plant width, single plant.*—About 12 cm.

*Lateral branch description.*—Length: About 12 cm. Width: About 4 mm. Internode length: About 5 mm. Aspect: Upright to outward. Strong: Strong. Texture: Smooth, glabrous. Color: 144B.

*Foliage description.*—Arrangement: Alternate, single; sessile. Leaves closely appressed and covering the lateral branches. Length: About 11 cm. Width: About 7 mm. Shape: Linear to narrowly oblanceolate. Margin: Entire. Apex: Acute. Base: Clasping. Texture, upper surface: Smooth, glabrous. Texture, lower surface: Pubescent. Venation pattern: Pinnate. Color: Developing leaves, upper surface: 147A. Developing leaves, lower surface: 194D. Fully expanded leaves, upper surface: 147A. Fully expanded leaves, lower surface: 198D. Venation, upper and lower surfaces: 147D.

Flowering description:

*Inflorescence form.*—Daisy-type composite inflorescence form. Inflorescences solitary. Ray and disc florets develop acropetally on a capitulum. Inflorescences circular in shape. Inflorescences not fragrant.

*Inflorescence longevity.*—Inflorescences last on the plant for about four to five days. Inflorescences persistent.

*Natural flowering season.*—Plants flower in the landscape from the spring until the fall; flowering continuous.

*Quantity of inflorescences.*—One open terminal inflorescence and about two inflorescence buds per lateral branch.

*Inflorescence aspect.*—Cupped.

*Inflorescence diameter.*—About 5 cm.

*Inflorescence depth (height).*—About 2.7 cm.

*Disc diameter.*—About 1.5 cm.

*Receptacle diameter.*—About 9 mm.

*Receptacle height.*—About 1.3 cm.

*Inflorescence buds.*—Length: About 1.6 cm. Diameter: About 8 mm. Shape: Ovoid. Color: 10A.

*Ray florets.*—Quantity per inflorescence: About 16 in a single whorl. Length: About 2.7 cm. Width: About 7 mm. Shape: Ligulate. Apex: Slightly emarginate. Base: Attenuate. Margin: Entire. Texture, upper and lower surfaces: Smooth, satiny. Color: When opening, upper surface: 12A. When opening, lower surface: 10A. Fully opened, upper surface: Towards the apex, 12A; towards the base, 17A. Fully opened, lower surface: 10A.

*Disc florets.*—Arrangement: Massed in the center of the receptacle. Quantity per inflorescence: About 96. Shape: Tubular with five lobes. Length: About 1.2 cm. Diameter, apex: About 1 mm. Diameter, base: Less than 1 mm. Color, immature: 3A. Color, mature: Towards the apex: 12A. Mid-section: 12C. Towards the base: 155D.

*Involucral bracts.*—Quantity per inflorescence: About 18 in two whorls. Shape: Needle-like; fused at base into a cup-like structure. Apex: Acute. Length: About 1.2 cm. Diameter: About 2 mm. Texture, upper and lower surfaces: Pubescent. Color, upper surface: 144A. Color, lower surface: 144B.

*Peduncle.*—Length: About 10.5 cm. Diameter: About 1.5 mm. Aspect: Erect. Strength: Strong. Texture: Very slightly pubescent. Color: 144C.

*Androecium.*—Present only on disc florets. Anther shape: Elongated, oval. Anther length: About 1.5 mm. Anther color: 14A. Amount of pollen: Scarce. Pollen color: 14A.

*Gynoecium.*—Present only on disc florets. Quantity per floret: One. Style length: About 7 mm. Style color: 14C. Stigma shape: Bi-parted. Stigma color: 14A. Ovary color: 157B.

*Seed/fruit.*—Seed and fruit development have not been observed.

Disease/pest resistance: Plants of the new *Gazania* have been observed to be relatively less susceptible to fungal pathogens common to *Gazanias*. Plants of the new *Gazania* have not been observed to be resistant to other pathogens or pests common to *Gazania*.

Temperature tolerance: Plants of the new *Gazania* have been observed to tolerate temperatures from −4 to 40° C.

It is claimed:

1. A new and distinct cultivar of *Gazania* named 'California Gold', as illustrated and described.

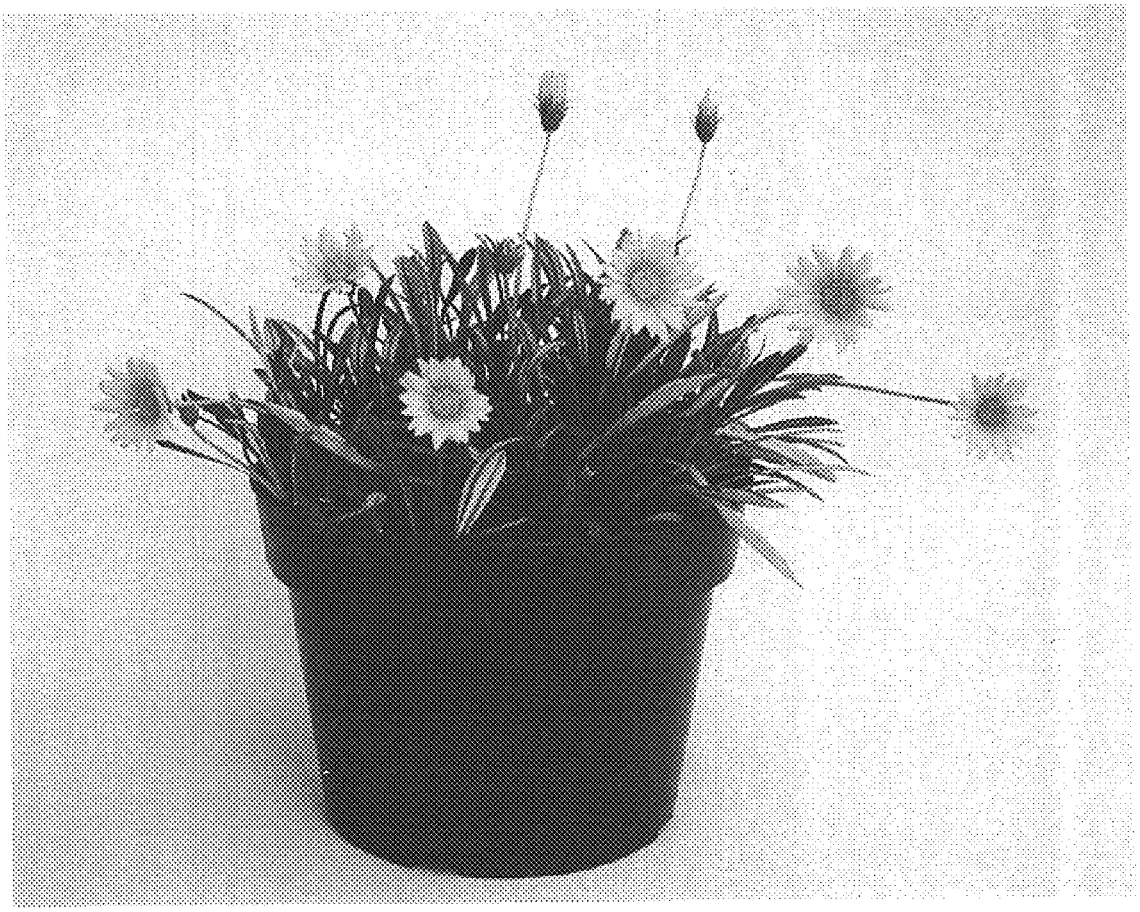
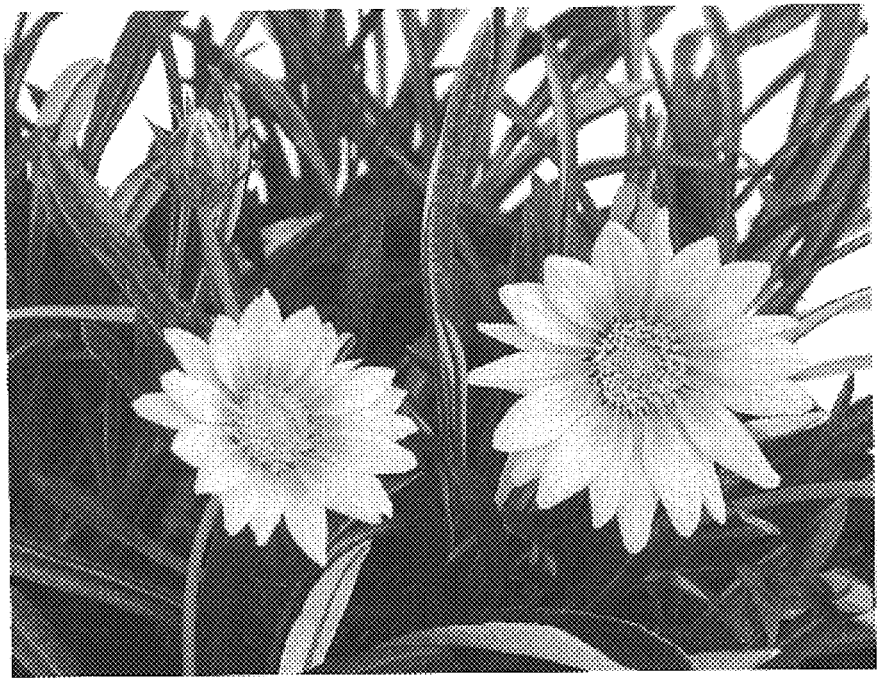

* * * * *